US008323974B2

(12) United States Patent
Davis et al.

(10) Patent No.: US 8,323,974 B2
(45) Date of Patent: *Dec. 4, 2012

(54) METHOD FOR EXCISION OF PLANT EMBRYOS FOR TRANSFORMATION

(75) Inventors: Brandon J. Davis, North Stonington, CT (US); Michael T. Mann, Groton, CT (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/098,781

(22) Filed: May 2, 2011

(65) Prior Publication Data

US 2012/0151626 A1 Jun. 14, 2012

Related U.S. Application Data

(60) Continuation of application No. 11/613,031, filed on Dec. 19, 2006, now Pat. No. 7,935,529, which is a division of application No. 10/911,191, filed on Aug. 4, 2004, now Pat. No. 7,150,993.

(60) Provisional application No. 60/493,011, filed on Aug. 5, 2003.

(51) Int. Cl.
*A01H 4/00* (2006.01)
*A01H 1/00* (2006.01)
*C12N 15/82* (2006.01)

(52) U.S. Cl. ............... 435/424; 435/430; 435/430.1; 800/298; 800/278; 536/26.1

(58) Field of Classification Search .................. None
See application file for complete search history.

(56) References Cited

U.S. PATENT DOCUMENTS

| | | |
|---|---|---|
| 1,849,786 A | 3/1932 | Bloede et al. |
| 3,104,692 A | 9/1963 | Turner |
| 3,301,292 A | 1/1967 | O'Connor |
| 3,667,523 A | 6/1972 | Lynn et al. |
| 4,066,012 A | 1/1978 | Satake et al. |
| 4,245,553 A | 1/1981 | Nakamura |
| 4,301,183 A | 11/1981 | Giguere |
| 4,326,358 A | 4/1982 | Lawrence et al. ............. 47/58 |
| 4,986,997 A | 1/1991 | Posner et al. ............... 426/622 |
| 5,004,863 A | 4/1991 | Umbeck |
| 5,015,580 A | 5/1991 | Christou et al. ........... 435/172.3 |
| 5,073,675 A | 12/1991 | Jones et al. .................. 800/205 |
| 5,164,310 A | 11/1992 | Smith et al. ............... 435/172.3 |
| 5,217,902 A | 6/1993 | Jones et al. .................. 800/205 |
| 5,250,313 A | 10/1993 | Giguere |
| 5,262,316 A | 11/1993 | Engler et al. ............. 435/172.3 |
| 5,286,635 A | 2/1994 | Hanson et al. ............. 435/172.3 |
| 5,368,778 A | 11/1994 | Shimotomai et al. |
| 5,379,952 A | 1/1995 | Geiger |
| 5,538,880 A | 7/1996 | Lundquist et al. ......... 435/172.3 |
| 5,550,318 A | 8/1996 | Adams et al. ................ 800/205 |
| 5,563,055 A | 10/1996 | Townsend et al. ......... 435/172.3 |
| 5,567,599 A | 10/1996 | Lemieux ................... 435/172.3 |
| 5,591,616 A | 1/1997 | Hiei et al. .................. 435/172.3 |
| 5,678,477 A | 10/1997 | Satake et al. |
| 5,693,512 A | 12/1997 | Finer et al. ................. 435/172.3 |
| 5,731,179 A | 3/1998 | Komari et al. ............. 435/172.3 |
| 5,767,366 A | 6/1998 | Sathasivan et al. |
| 5,824,877 A | 10/1998 | Hinchee et al. .............. 800/205 |
| 5,846,797 A | 12/1998 | Strickland |
| 5,914,451 A | 6/1999 | Martinell et al. ............ 800/300 |
| 5,952,230 A | 9/1999 | Kim et al. .................... 435/415 |
| 5,981,840 A | 11/1999 | Zhao et al. ................... 800/294 |
| 6,070,815 A | 6/2000 | Miyatake ........................ 241/47 |
| 6,140,555 A | 10/2000 | Reichert et al. .............. 800/293 |
| 6,153,813 A | 11/2000 | Reichert et al. .............. 800/293 |
| 6,265,638 B1 | 7/2001 | Bidney et al. ................ 800/294 |
| 6,307,127 B1 | 10/2001 | Jorsboe et al. ............... 800/294 |
| 6,384,301 B1 | 5/2002 | Martinell et al. ............ 800/294 |
| 6,422,137 B1 | 7/2002 | Nakhei-Nejad ................ 99/621 |
| 6,900,057 B2 | 5/2005 | Burns et al. |
| 6,936,294 B2 | 8/2005 | Matthews et al. |
| 7,002,058 B2 | 2/2006 | Martinell et al. ............ 800/294 |
| 7,057,089 B2 | 6/2006 | Ranch et al. ................ 800/320.1 |
| 7,150,993 B2 * | 12/2006 | Davis et al. .................. 435/424 |
| 7,279,336 B2 | 10/2007 | Gelvin et al. ................ 800/294 |
| 7,288,694 B2 | 10/2007 | Armstrong et al. ........... 800/278 |
| 7,402,734 B2 | 7/2008 | Martinell et al. ............ 800/287 |
| 7,560,611 B2 * | 7/2009 | Adams et al. ................ 800/278 |
| 7,658,033 B2 | 2/2010 | Martinell et al. ........ 47/58.1 SE |
| 7,694,457 B2 | 4/2010 | Martinell et al. ........ 47/58.1 SE |
| 7,888,552 B2 | 2/2011 | Ye et al. ...................... 800/278 |
| 7,935,529 B2 * | 5/2011 | Davis et al. .................. 435/424 |
| 7,937,890 B2 | 5/2011 | Adams et al. ................. 47/58.1 |

(Continued)

FOREIGN PATENT DOCUMENTS

CN 1302900 A 7/2001

(Continued)

OTHER PUBLICATIONS

Matthys-Rochon, "In vitro development of maize immature embryos: a tool for embryogenesis analysis," *Journal of Experimental Botany* 49(322):839-845, 1998.
U.S. Appl. No. 12/045,498, filed Mar. 10, 2008, Calabotta et al.
U.S. Appl. No. 12/045,502, filed Mar. 10, 2008, Dersch et al.
U.S. Appl. No. 12/045,562, filed Mar. 10, 2008, Martinell et al.
Aragao et al., "Germ line genetic transformation in cotton (*Gossypium hirsutum* L. by selection of transgenic meristematic cells with a herbicide molecule," *Plant Sci.*, 168(5):1227-1233, 2005.
Bechtold et al., "The maternal chromosome set is the target of the T-DNA in the in planta transformation of *Arabidopsis thaliana*," *Genetics*, 155:1875-1887, 2000.
Bouchez et al., "A binary vector based on basta resistance for in planta transformation of *Arabidopsis thaliana*," *Comptes Rendus des Seances de L'Academie des Sciences*, Series II: Sciences de la Vie, 316(1):1188-1193, 1993.

(Continued)

*Primary Examiner* — Brent T Page
(74) *Attorney, Agent, or Firm* — SNR Denton US LLP; Thomas P. McBride Esq.

(57) ABSTRACT

This invention describes a simple method useful for the excision and isolation of maize immature embryos. The embryos are useful for plant tissue culture and transformation methods.

17 Claims, 2 Drawing Sheets

U.S. PATENT DOCUMENTS

| | | | |
|---|---|---|---|
| 2002/0088383 A1 | 7/2002 | Barry et al. | |
| 2002/0120961 A1 | 8/2002 | Ranch et al. | 800/293 |
| 2002/0184663 A1 | 12/2002 | Sun et al. | |
| 2003/0074686 A1 | 4/2003 | Heinz et al. | 800/294 |
| 2004/0034889 A1 | 2/2004 | Khan | 800/294 |
| 2005/0005321 A1 | 1/2005 | Martinell et al. | 800/287 |
| 2005/0032224 A1 | 2/2005 | Davis et al. | 435/424 |
| 2005/0042305 A1 | 2/2005 | Endo et al. | 424/725 |
| 2005/0044595 A1 | 2/2005 | Arias et al. | 800/294 |
| 2005/0158699 A1 | 7/2005 | Kadkade et al. | |
| 2005/0183170 A1 | 8/2005 | Fillatti et al. | 800/278 |
| 2005/0246786 A1 | 11/2005 | Adams et al. | 800/278 |
| 2006/0005273 A1 | 1/2006 | Rudrabhatla et al. | 800/278 |
| 2006/0059589 A1 | 3/2006 | Martinell et al. | 800/294 |
| 2006/0196369 A1 | 9/2006 | Feazel et al. | |
| 2006/0260012 A1 | 11/2006 | Khan | 800/294 |
| 2007/0039075 A1 | 2/2007 | Tissot et al. | 800/278 |
| 2007/0157346 A1 | 7/2007 | Davis et al. | 435/424 |
| 2007/0271627 A1 | 11/2007 | Ye et al. | 800/278 |
| 2008/0179435 A1 | 7/2008 | Martinell et al. | 47/58.1 SE |
| 2008/0182330 A1 | 7/2008 | Martinell et al. | 47/58.1 SE |
| 2008/0256667 A1 | 10/2008 | Dersch et al. | 800/278 |
| 2008/0280361 A1 | 11/2008 | Calabotta et al. | 800/278 |
| 2009/0029449 A1 | 1/2009 | Adams et al. | 435/285.1 |
| 2011/0271410 A1 | 11/2011 | Adams et al. | |

FOREIGN PATENT DOCUMENTS

| | | |
|---|---|---|
| CN | 1838995 A | 9/2006 |
| EP | 0298722 | 1/1989 |
| EP | 0 339 577 | 11/1989 |
| EP | 0 356 987 | 3/1990 |
| EP | 0 380 055 | 8/1990 |
| EP | 0740897 B1 | 11/1999 |
| EP | 0958863 | 11/1999 |
| EP | 1142489 | 10/2001 |
| EP | 1 236 801 | 9/2002 |
| GB | 402848 | 12/1933 |
| GB | 439399 | 12/1935 |
| GB | 657644 | 9/1951 |
| GB | 861711 | 2/1961 |
| GB | 1459551 | 12/1976 |
| JP | 59-082063 | 5/1984 |
| JP | 10-276748 | 10/1998 |
| JP | 11-164678 | 6/1999 |
| JP | 017107 | 1/2001 |
| JP | 292717 | 10/2001 |
| JP | 2002-119886 A | 4/2002 |
| JP | 2003-339395 | 12/2003 |
| JP | 2004-357547 | 12/2004 |
| WO | WO 92/15675 | 9/1992 |
| WO | WO 95/06722 | 9/1995 |
| WO | WO 96/10341 | 4/1996 |
| WO | WO 98/01575 | 1/1998 |
| WO | WO 99/02267 | 1/1999 |
| WO | WO 99/10513 | 3/1999 |
| WO | WO 99/20776 | 4/1999 |
| WO | WO 00/42207 | 7/2000 |
| WO | WO 01/29241 | 4/2001 |
| WO | WO 02/00010 | 1/2002 |
| WO | WO 02/37987 | 5/2002 |
| WO | WO 02/066599 | 8/2002 |
| WO | WO 03/017752 | 3/2003 |
| WO | WO 03/100381 | 12/2003 |
| WO | WO 2004/000006 | 12/2003 |
| WO | WO 2005/000471 | 1/2005 |
| WO | WO 2005/122750 | 12/2005 |
| WO | WO 2006/026466 | 3/2006 |
| WO | WO 2007/079538 | 7/2007 |
| WO | WO 2007/103769 | 9/2007 |

OTHER PUBLICATIONS

Bretagne-Sagnard et al., "Selection of transgenic flax plants is facilitated by spectinomycin," *Transgenic Res.*, 5:131-137, 1996.

Broothaerts et al., "Gene transfer to plants by diverse species of bacteria," *Nature*, 433:629-633, 2005.

Chai et al., "Optimum moisture content of seeds stored at ambient temperatures," *Seed Science Research*, 8(Supp. 1):23-23, 1998.

Chaudhary et al., "Slow desiccation leads to high-frequency shoot recovery from transformed somatic embryos of cotton (*Gossypium hirsutum* L. cv. Coker 310 FR)," *Plant Cell Rep.*, 21:955-960, 2003.

Chen, Database WPI Week 200432, Oct. 21, 2003.

Finer et al., "Transformation of soybean via particle bombardment of embryogenic suspension culture tissue," *In Vitro Cell. Dev. Biol.*, 27P:175-182, 1991.

Francois et al., "Different approaches for multi-transgene-stacking in plants," *Plant Sci.*, 163:281-295, 2002.

Green et al., "Plant regeneration from tissue cultures of maize," *Crop Sci.*, 15:417-421, 1975.

Haris et al, "Transformation of cotton (*Gossypium hirsutum* L.) with insect resistant gene by particle bombardment and agrobacterium," *Pakl. J. of Biological Sci.*, 1(3):170-174, 1998.

Hewezi et al., "Dehydrating immature embryo split apices and rehydrating with *Agrobacterium tumefaciens*: A new method for genetically transforming recalcitrant sunflower," *Plant Mol. Biol. Reporter*, 20:335-345, 2002.

Hinchee et al., "Production of transgenic soybean plants using *Agrobacterium*-mediated DNA transfer," *Bio/Technology*, 6:915-922, 1988.

Hussain et al., "Sonication assisted *Agrobacterium* mediated transformation (SAAT): An alternative method for cotton transformation," *Pak J. Bot.*, 39(1):223-230, 2007.

Jones et al., "Effective vectors for transformation, expression of heterologous genes, and assaying transposon excision in transgenic plants," *Transgenic Res.*, 1:285-297, 1992.

Kofer et al., "PEG-mediated plastid transformation in higher plants," *In Vitro Cell Dev. Biol.—Plant*, 34:303-309, 1998.

Krysan, "Ice-Cap. A high-throughput method for capturing plant tissue samples for genotype analysis," *Plant Physiology*, 135:1162-1169, 2004.

Kumar et al., "Stable transformation of the cotton plastid genome and maternal inheritance of transgenes," *Plant Mol. Biol.*, 56:203-216, 2004.

Kumlehn et al., "In vitro development of wheat (*Triticum aestivum* L.) from zygote to plant via ovule culture," *Plant Cell Reports*, 16:663-667, 1997.

Lacorte et al., "Transient expression of GUS and the 2S albumin gene from Brazil nut in peanut (*Arachis hypogaea* L.) seed explants using particle bombardment," *Plant Cell Reports*, 16:619-623, 1997.

Larkin et al., "Transgenic white clover. Studies with the auxin-responsive promoter, GH3, in root gravitropism and lateral root development," *Transgenic Research*, 5:325-335, 1996.

Laurie et al., "A novel technique for the partial isolation of maize embryo sacs and subsequent regeneration of plants," *In Vitro Cellular and Development Biology—Plant*, 35(4):320-325, 1999.

Li et al., "Improvement of cotton fiber quality by transforming the acsA and acsB genes into *Gossypium hirsutum* L. by means of vacuum infiltration," *Plant Cell Rep.*, 22:691-697, 2004.

Lim et al., "Construction of small binary vectors for *Agrobacterium*-mediated transformation in plants," *J. of Plant Biol.*, 42(4):317-320, 1999.

Lim et al., "Expression of the glutathione S-transferase gene (NT107) in transgenic dianthus superbus," *Plant Cell, Tissue and Organ Culture*, 80:277-286, 2005.

Lowe et al., "Germline transformation of maize following manipulation of chimeric shoot meristems," *Bio/Technology*, 13:677-682, 1995.

McCabe et al., "Stable transformation of soybean (Glycine max) by particle acceleration," *Bio/Technology*, 6:923-926, 1988.

McCabe et al., "Transformation of elite cotton cultivars via particle bombardment of meristems," *Bio/Technology*, 11:596-598, 1993.

Miki et al., "Procedures for introducing foreign DNA into plants," In: Methods in Plant Molecular Biology and Biotechnology, Glick et al. (Eds.), CRC Press, Inc., Boca Raton, FL, pp. 67-88, 1983.

Oreifig et al., "Development of a non-lethal selection system by using the aadA marker gene for efficient recovery of transgenic rice (*Oryza sativa* L.)," *Plant Cell Reports*, 22:490-496, 2004.

Patnaik et al., "*Agrobacterium*-mediated transformation of mature embryos of *Triticum aestivum* and *Triticum durum*," *Current Sci.*, 91(3):307-317, 2006.

Paz et al., "Improved cotyledonary node method using an alternative explant derived from mature seed for efficient *Agrobacterium*-mediated soybean transformation," *Plant Cell Rep.*, 25:206-213, 2006.

PCT Search Report for Application No. PCT/US2008/056411 dated Oct. 2, 2008.

Popelka et al., "Genetic transformation of cowpea (*Vigna unguiculata* L.) and stable transmission of the transgenes to progeny," *Plant Cell Rep.*, 25:304-312, 2006.

Rohini et al., "Transformation of peanut (*Arachis hypogaea* L.): a non-tissue culture based approach for generating transgenic plants," *Plant Sci.*, 150:41-49, 2000.

Sandvang, "Novel streptomycin and spectinomycin resistance gene as a gene cassette within a class 1 integron isolated from *Escherichia coli*," *Antimicrobial Agents and Chemotherapy*, 43(12):3036-3038, 1999.

Schnall et al., "Culturing peanut (*Arachis hypogaea* L.) zygotic embryos for transformation via microprojectile bombardment," *Plant Cell Reports*, 12:316-319, 1993.

Schnug et al., "Preparation techniques of small sample sizes for sulphur and indirect total glucosinolate analysis in *Brassica* seeds by X-Ray fluorescence spectroscopy," *Fett Sci. Technol.*, 95(9):334-337, 1993.

Schroder et al., "Transformation of *Brassica napus* by using the aadA gene as slectable marker and inheritance studies of the marker genes," *Physiologia Plantarum*, 92:37-46, 1994.

Senaratna et al., "Dehydration injury in germinating soybean (glycine max L. merr.) seeds," *Plant Physiology*, 72:620-624, 1983.

Simoens et al., "A binary vector for transferring genomic libraries to plants," *Nucleic Acids Research*, 14(20):8073-8090, 1988.

"Study of tissue culture of immature embryos and plant regeneration in maize," *Journal of Sichuan University (Natural Science Edition)*, 36(6):1125-1126, Abstract, 1999. (English Translation).

Svab et al., "Aminoglycoside-3"—adenyltransferase confers resistance to spectinomycin and streptinomycin in *Nicotiana tabacum*," *Plant Mol. Biol.*, 14:197-205, 1990.

Svab et al., "High-frequency plastid transformation in tobacco by selection for a chimeric aadA gene," *Proc. Natl. Acad. Sci. USA*, 90:913-917, 1993.

Trick et al., "SAAT: sonication-assisted *Agrobacterium*-mediated transformation," *Transgenic Research*, 6:329-336, 1997.

Vertucci et al., "Theoretical basis of protocols for seed storage," *Plant Physiology*, 94:1019-1023, 1994.

Von Post et al., "A high-throughput DNA extraction method for barley seed," *Euphytica*, 130:255-260, 2003.

Wang et al., "Maize (*Zea mays*) genetic transformation by co-cultivating germinating seeds with *Agrobacterium tumefaciens*," *Biotechnol. Appl. Biochem*, 46:51-55, 2007.

Xue et al., "A multi-needle-assisted transformation of soybean cotyledonary node cells," *Biotechnol. Lett.*, 28:1551-1557, 2006.

Zambre et al., "Light strongly promotes gene transfer from *Agrobacterium tumefaciens* to plant cells," *Planta*, 216(4):580-586, 2003.

Preliminary Amendment filed in U.S. Appl. No. 12/192,932, dated Sep. 19, 2008.

Notice of Allowance regarding U.S. Appl. No. 12/192,932, dated Aug. 5, 2010.

Aitken-Christie et al., "Automation and Environmental Control in Plant Tissue Culture," *Kluwer Academic Publishers*, Netherlands, 1995.

Birch, R. G., "Plant Transformation: Problems and Strategies for Practical Application," *Annu. Rev. Plant Physiol. Plant Mol. Biol.*, 48:297-326, 1997.

Buchheim et al., "Maturation of Soybean Somatic Embryos and the Transition of Plantlet Growth" *Plant Physiol.*, 89:768-775, 1989.

Chandra et al., "Regeneration and genetic transformation of grain legumes: An overview," *Current Science*, 84:(3)381-387, 2003.

Chen et al., "A comparison of methods for delivering DNA to wheat: The application of wheat dwarf virus DNA to seeds with exposed apical meristems," *Transgenic Res.*, 1:93-100, 1992.

Chen et al., "Factors influencing *Agrobacterium*-mediated transformation of monocotyledonous species," *In Vitro Cell Dev. Biol.*, 40:31-45, 2004.

Chengalrayan et al., "High-frequency conversion of abnormal peanut somatic embryos," *Plant Cell Reports*, 16:783-786, 1997.

Delporte et al., "Plant regeneration through callus initiation from thin mature embryo fragments of wheat," *Plant Cell, Tissue and Organ Culture*, 67:73-80, 2001.

Grandison et al., "Separation Process in the Food and Biotechnology Industries, Principles and Applications," *Woodhead Publishing Limited*, 266-286, 1995.

Ibaraki et al., "Automation of somatic embryo production," *Plant Cell, Tissue and Organ Culture*, 65:179-199, 2001.

Johnston et al., "Mass Isolation of Viable Wheat Embryos," *Nature*, 179:160-161, 1957.

Kern, "Comparison between Wheat Embryos Isolated Mechanically and by Floating off from Organic Solvents," *Biologia Plantarum (PRAHA)*, 17(4):309-313, 1975.

Kingsley, "Introductory Plant Biology," *The McGraw-Hill Companies Inc.*, Eighth Edition, 2000.

Livingstone et al., "Efficient transformation and regeneration of diverse cultivars of peanut (*Arachis hypogaea* L.) by particle bombardment into embryogenic callus produced from mature seeds," *Molecular Breeding*, 5:43-51, 1999.

Mahalakshmi et al., "Exogenous DNA Uptake via Cellular Permeabilization and Expression of Foreign Gene in Wheat Zygotic Embryos," *Plant Biotechnology*, 17(3)235-240, 2000.

Malone-Schoneberg et al., "Stable transformation of sunflower using *Agrobacterium* and split embryonic axis explants," *Plant Science*, 103:199-207, 1994.

Marcus et al., "The Wheat Embryo Cell-Free System," *Methods of Enzymology*, 30:749-754, 1974.

McKersie et al., "Application of artificial seed technology in the production of hybrid alfalfa (*Medicage sativa* L.)," *In Vitro Cell Dev. Biol.*, 25:1183-1188, 1989.

Nghi et al., "Performance of a plate mill and a modified Engelberg huller for small-scale dry milling and de-germing of maize," *International Journal of Food Science and Technology*, 29:347-353, 1994.

Notice of Opposition regarding European Patent No. 1,635,949, dated Oct. 5, 2011.

Orlikowska et al., "Effect of in vitro storage at 4° C on survival and proliferation of two apple root stock," *Plant Cell, Tissue and Organ Culture*, 31:1-7, 1992.

Pollard et al., "Plant and Cell Tissue Culture," *Methods in Molecular Biology*, vol. 6, 1990.

Sawahel et al., "Stable Genetic Transformation of Mature Wheat Embryos using Silicone Carbide Fibers and DNA Imbibition," *Cellular and Molecular Biology Letters*, 2:421-429, 1997.

Senaratna et al., "Atrificial seeds of alfalfa (*Medicago sativa* L.) induction of desiccation tolerance in somatic embryos," *In Vitro Dev. Biol.*, 26:85-90, 1990.

Senaratna et al., "Desiccation tolerance of alfalfa (*Medicago sativa* L.) somatic embryos. Influence of abscisic acid, stress pretreatments and drying rates," *Plant Sci.*, 35:253-259, 1989.

Senaratna et al., "Direct DNA uptake during the imbibition of dry cells," *Plant Sci.*, 79:223-228, 1991.

Sheilds et al., "Use of fungicides in plant tissue culture," *Plant Cell Reports*, 3:33-36, 1984.

Statement from Dr. William J. Gordon-Kamm, Sep. 13, 2011.

Tang et al., "Regeneration of transgenic loblolly pine (*Pine taeda* L.) from zygotic embryos transformed with *Agrobacterium tumefaciens*," *Planta*, 213:981-989, 2001.

Töpfer et al., Uptake and Transient Expression of Chimeric Genes in Seed-Derived Embryos, *The Plant Cell*, 1:133-139, 1989.

Wilcox, "Soybeans: Improvement, Production, and Uses," *American Society of Agronomy, Crop Science Society of America, Soil Science of America*, 1987.

WPI Week Database No. TW558420, dated Oct. 21, 2003.

Moon et al., "Effects of proliferation, maturation, and desiccation methods on conversion of soybean somatic embryos", *In vitro Cellular & Developmental Biology—Plant* 39(6):623-628, 2003.

Abdelnour-Esquivel et al., "Cryopreservation of zygotic embryos of coffea spp", *Cryo Letters* 13(5):297-302, 1992.

English translation of office action issued in Chinese Patent Application No. 200880007599.4 on Aug. 10, 2011.

Higley et al., "Effects of non-destructive tissue extraction on the viability of corn, soybean, and bean seeds", *Seed Science and Technology*, 22(2):245-252, 1994.

Office action dated Mar. 9, 2012, in European Patent Application No. 08731808.5.

* cited by examiner

METHOD FOR EXCISION OF PLANT EMBRYOS FOR TRANSFORMATION

REFERENCE TO PRIOR APPLICATION

This application is a continuation of U.S. patent application Ser. No. 11/613,031, filed Dec. 19, 2006, now issued as U.S. Pat. No. 7,935,529; which is a divisional application of Ser. No. 10/911,191, filed Aug. 4, 2004, now issued as U.S. Pat. No. 7,150,993; which claims benefit of U.S. Provisional Application Ser. No. 60/493,011, filed Aug. 5, 2003, the entire disclosures of which are each specifically incorporated herein by reference.

FIELD OF THE INVENTION

Disclosed herein is a method for the vacuum excision of explant tissue from plants. The method is particularly useful for isolating immature embryogenic tissue for propagation and regeneration of a plant. More particularly, the method is useful for the production of a transgenic plant.

The preparation of embryogenic tissue for plant propagation, regeneration and transformation is time consuming and labor intensive, especially as it involves manual excision of desired explant tissue. For example, in corn the manual removal of individual immature embryos is a common means for isolating tissue useful for experiments. The manual excision of embryogenic tissues is not only laborious, it is fraught with ergonomic issues. It would be of great benefit to the art of plant propagation, regeneration and transformation to have a method of excising embryogenic tissue that is rapid and reduces ergonomic burden on the user.

An object of this invention is to provide a simple method for the isolation of explant tissue. More particularly, the invention provides a method directed to the use of a vacuum to isolate individual immature embryos from an ear of corn.

SUMMARY OF THE INVENTION

This invention provides a simple method for the vacuum excision of a plant embryo. The method is useful for isolating immature maize embryos from ears of corn.

Vacuum excision may be carried out using an aspirator which, in its simplest terms, is an isolation tube connected to a collecting receptacle having a vacuum source. The aspirator is used to vacuum excise and collect an immature embryo from a kernel, for example, the isolation of a maize immature embryo from a kernel. In one embodiment, the maize kernel is on an ear. Each immature embryo may be intact or partial and may be accompanied by endosperm material. Each immature embryo, either partial or intact, is useful for the production of callus tissue and the regeneration of a fertile maize plant. Vacuum excision is also used to isolate a slurry comprising both partial and intact immature embryos. The slurry is useful for the production of callus tissue and regeneration of a fertile maize plant.

Each immature embryo, either partial or intact, or the slurry comprising both partial and intact immature embryos, is also useful for transformation. An intact immature embryo may be directly transformed shortly after excision, propagated and regenerated into a transgenic plant. Alternatively, an intact immature embryo, partial immature embryo, or slurry comprising both partial and intact immature embryos, may be propagated into callus material that may be used for transformation and regenerated into a fertile, transgenic maize plant.

BRIEF DESCRIPTION OF THE DRAWINGS

FIG. 2 is an illustration of an in-line sieving unit.

DETAILED DESCRIPTION OF THE INVENTION

Figure 1:
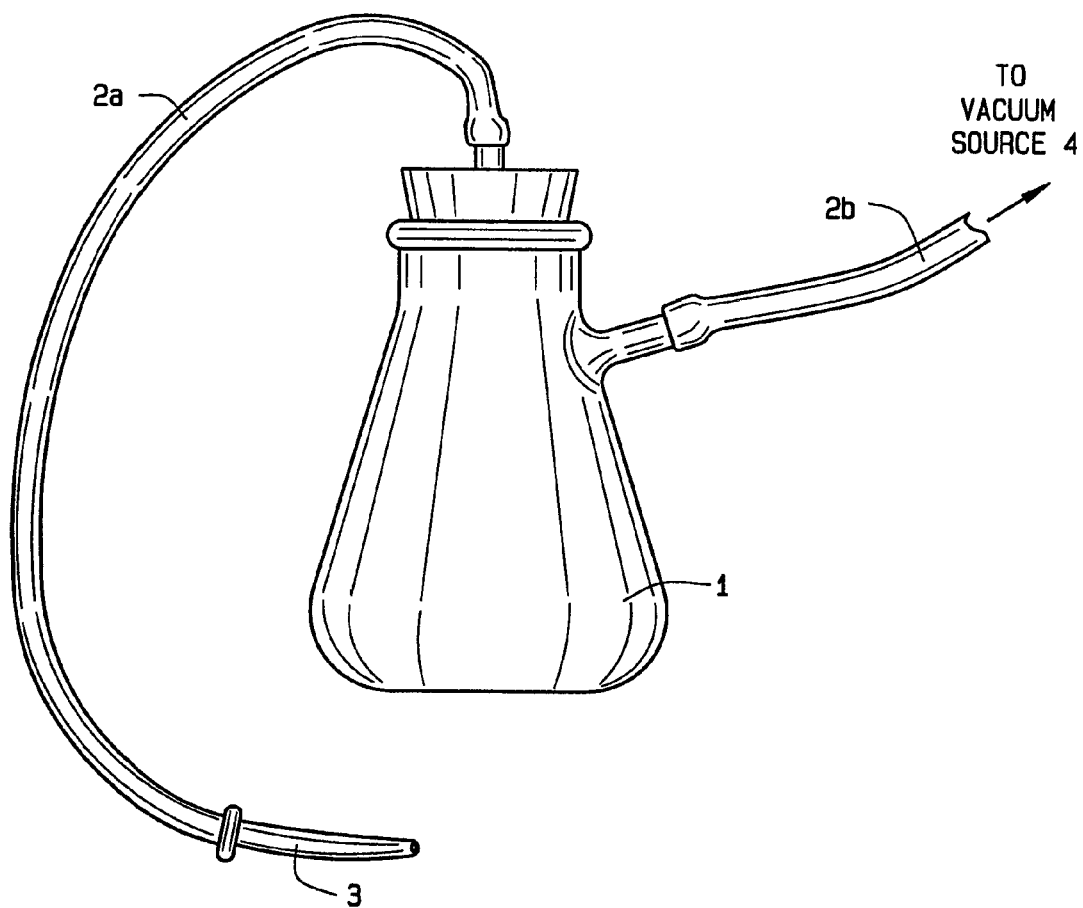
FIG. 1 is an illustration of an aspirator useful for vacuum excision of immature embryos.

This invention provides a novel method for the removal of an embryogenic tissue explant for the propagation of tissue and regeneration of a plant. Preferably, the method is used with monocot plants including, but not limited to, maize, wheat and rice. In particular, the method is used for the isolation of tissue for use with transformation methods. The method is particularly useful for the isolation of immature embryos (IEs) from any variety of maize, for the propagation of tissue and regeneration of a maize plant, and more particularly, for the production of a stably transformed maize plant.

As used herein "tissue explant" or "explant tissue" is a first tissue, such as an immature embryo, isolated away from a second tissue, such as a corn kernel, wherein the isolated tissue is useful for the propagation of a plant cell, the maintenance of callus and/or for the regeneration of a plant. The explant or a cell derived therefrom may be used for transformation purposes and may be transformed by any plant transformation method, preferably by *Agrobacterium* or particle bombardment. As used herein "propagation" is the maintenance of viable plant cells on a media, e.g. a callus tissue on a solid medium or protoplasts in liquid medium. During propagation, the plant cells are usually dividing and producing an increasing number of cells or amount of tissue.

As used herein "regeneration" means the process of growing a plant from a plant cell (e.g., plant protoplast, callus or immature embryo). It is contemplated that any cell from which a fertile plant may be regenerated is useful for propagation or as a recipient cell for transformation. Callus may be initiated from tissue sources including, but not limited to, immature embryos, seedling apical meristems, microspores and the like. Those cells that are capable of proliferating as callus also are recipient cells for genetic transformation. Preferably, the plant is fertile when fully regenerated.

For purposes of this invention, "kernel" means a tissue of a monocot plant that comprises an immature embryo along with endosperm tissue, for example a maize kernel or a grain of wheat or rice. Typically, there is a single immature embryo per kernel. In maize, kernels are located on what is termed an ear; in wheat or rice, kernels are located on what is termed a head. Immature embryos are typically isolated from maize at approximately 10 to 14 days post pollination and may range in size from about 1 mm to about 4 mm in the largest dimension (commonly called "length"). Isolated immature embryos of about 1.5 mm to about 2.5 mm are preferred for use in many plant propagation and transformation methods.

An intact immature embryo is an embryo which, when isolated from a kernel, is whole in nature; it comprises all of its natural parts in one piece, organized as they naturally occur in the kernel. A partial immature embryo is an embryo which, when isolated from a kernel, is not whole in nature. For example, the partial immature embryo may be broken into one or more pieces during the excision process and may not comprise all of its natural parts in one piece. As used herein, a tissue is said to be "embryogenic" if the cells of the tissue are capable of cell division such that the amount of tissue increases and/or the tissue that is formed is embryonic tissue. Immature embryos are an example of an embryogenic tissue.

The vacuum excision of the invention may be carried out using any type of suitable vacuum excision apparatus such as the exemplary device shown in FIG. 1. Referring to FIG. 1, the size of the collecting receptacle 1 used to collect the immature embryos may vary; in one embodiment the collecting receptacle 1 is a 125 ml side-arm flask. A first piece of tubing 2a is used for connecting an isolation tube 3 to the collecting receptacle 1 and a second piece of tubing 2b is used for connecting the collecting receptacle 1 to the vacuum source 4. The pieces of tubing 2a and 2b may vary in diameter and length to accommodate excision of an immature embryo from a monocot kernel. In one embodiment, a useful inner diameter of tubing 2a and 2b is about 6 mm. Attached to the first piece of tubing 2a is the isolation tube 3 for extracting the immature embryo. Tubing 2a used to connect the collecting receptacle 1 to the isolation tube 3 can be any convenient length; for example, about 34 cm to about 42 cm is useful.

The isolation tube 3 is preferably a tube with a tapered end; more preferably the isolation tube 3 used to extract the embryos is a wide-bore pipette tip. The diameter of aperture of the isolation tube 3 may vary; in one embodiment, the aperture diameter of the isolation tube 3 may range from about 1.5 mm to about 4 mm, preferably an isolation tube 3 with an aperture diameter of about 2.5 mm is used. The aperture of the isolation tube 3 should be varied to accommodate the size of the embryos being isolated, with a larger aperture being used to isolate larger embryos. For example, an isolation tube 3 with an aperture diameter of about 2.5 mm can be used to isolate immature embryos of about 2.5 mm or smaller.

The amount of vacuum applied from a vacuum source 4 to the collecting receptacle 1 may vary; any vacuum that causes the excision and removal of the immature embryo from the kernel is within the scope of the invention. Useful vacuum may range from about 500 to about 740 mm Hg; preferably from about 525 to about 740 mm Hg, even more preferably from about 550 to about 740 mm Hg; most preferably, about 610 to about 740 mm Hg is used to isolate embryos. One skilled in the art would know that it would be possible to change the size of the collecting receptacle 1, the diameter of the tubing 2a and 2b, the length of the tubing 2a and 2b, the diameter or length of the isolation tube 3 or pipette tip used to extract the embryos, and the vacuum applied to achieve vacuum isolation of immature embryos from maize.

In one embodiment, the immature embryos are drawn into a collecting receptacle 1 into a liquid solution such as cell growth media. Alternatively, the embryos are drawn into a collecting receptacle 1 fitted to contain a support to catch the embryos. This support may be a solid or semi-solid medium, felt, cotton packing, mesh, a sieve or a combination of supports to catch the embryos as they are received into the collecting receptacle 1. In another embodiment, the embryos are drawn up into the isolation tube 3 and, rather than be collected in the collecting receptacle 1, the vacuum is reversed and pressure is used to push the embryos out for collection, for example, onto a plate of solid or semi-solid medium.

Figure 2A:
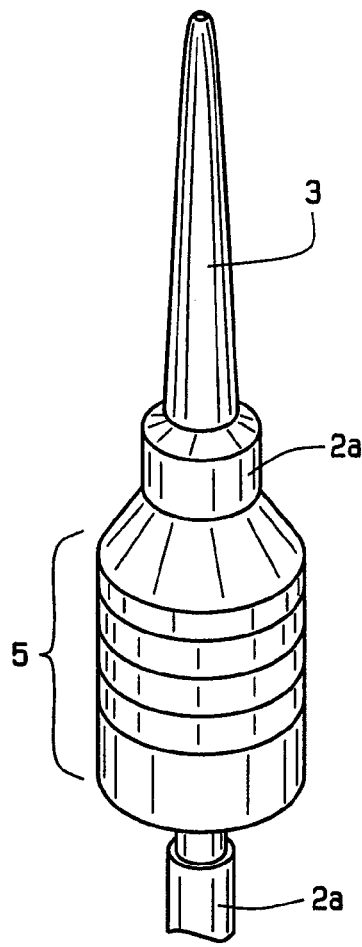
FIG. 2A shows the unit in one piece and FIG. 2B shows the sections of the unit.
Figure 2B:
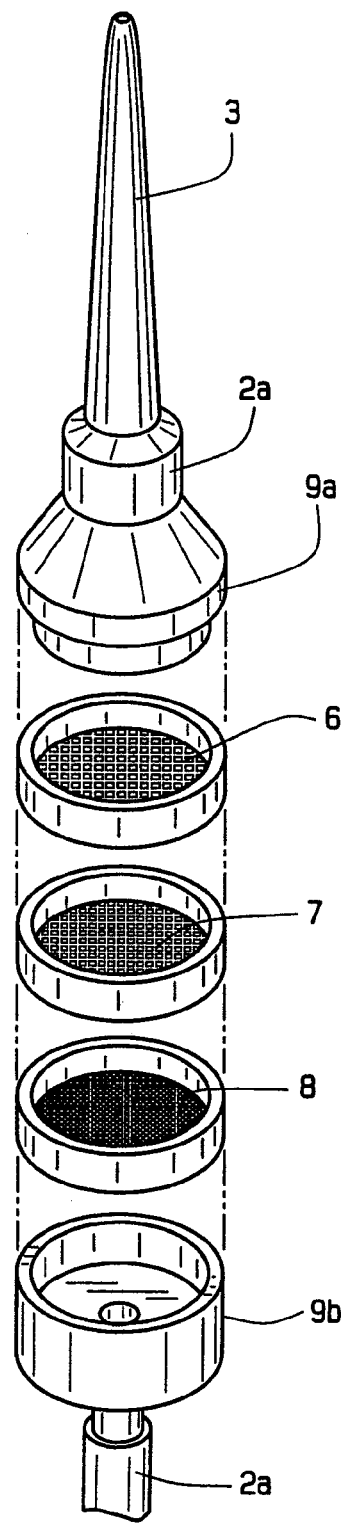

With reference to FIGS. 2A and 2B, an in-line sieving unit 5 is placed in the line of the first piece of tubing 2a connecting the isolation tube 3 to the collecting receptacle 1 such that embryos are collected on a mesh or sieving material rather than in the collecting receptacle 1 and retrieved therefrom. In one embodiment, several layers of mesh are used in the in-line sieving unit 5, with the mesh size decreasing with distance from the isolation tube 3. In one embodiment, the in-line sieving unit 5 is assembled from sections of nominal two inch tubing and comprises three layers of autoclavable, stainless steel sieving material, each layer being separated by approximately 1.3 cm and the layers of sieving material are joined to the tubing 2a via connectors 9a and 9b. In one embodiment, the layer of sieving material 6 nearest to the isolation tube 3 has openings of about 1130 microns, the middle layer of sieving material 7 has openings of about 979 microns and the layer of sieving material 8 has openings of about 472 microns. Embryos are collected on any layer of the sieving materials 6 and 7 and 8 and are manually retrieved or washed off the sieving material 6 and 7 and 8 by a gentle stream of liquid, such as media, for further use. In another embodiment, the layers of sieving material 6 and 7 and 8 may be altered such that only one or two layers are used, or that four or more layers are used, or that any two layers are of the same type of sieving material. One skilled in the art would know that the diameter or length of the in-line sieving unit 5, position within the tubing 2a, opening sizes of the sieving material 6 and 7 and 8 and number of sieving material layers 6 and 7 and 8 may be varied and still achieve vacuum isolation of immature embryos from maize.

It is believed that this method may be applicable to all kinds of plants for the isolation of one tissue from another, including but not limited to separating a first dicot tissue from a second dicot tissue or a first monocot tissue from a second monocot tissue. For example, vacuum isolation is useful to simply isolate the seeds of a plant from a floral structure, such as, but not limited to, the isolation of mature seeds from a mixture of soybean seeds and seed pods. In another example, vacuum isolation is useful to isolate embryonic tissue from other tissues. Alternatively, vacuum excision is useful to separate mixed tissues contained within a slurry, such as the isolation of monocot immature embryos from a slurry comprising immature embryos, endosperm and various other kernel tissues. As exemplified in the present invention, vacuum isolation is useful to isolate maize immature embryos from kernels on an ear.

Recombinant DNA Constructs—When transformation of the tissue explant is carried out, the present invention contemplates the use of any DNA molecule capable of imparting any desired attribute to a plant, including but not limited to herbicide resistance or tolerance, insect resistance or tolerance, disease resistance or tolerance (viral, bacterial, fungal, nematode), stress tolerance and/or resistance, as exemplified by resistance or tolerance to drought, heat, chilling, freezing, excessive moisture, salt stress and oxidative stress, increased yield, food or feed content and value, physical appearance, male sterility, drydown, standability, prolificacy, starch quantity and quality, oil quantity and quality, protein quality and quantity, amino acid composition, and the like.

Genes for imparting such desired characteristics are assembled in recombinant DNA constructs using methods known to those of ordinary skill in the art. Standard cloning techniques are useful for building DNA constructs and vectors suitable for use in the transformation of plant cells. One such technology for building DNA constructs and vectors for transformation is the GATEWAY™ cloning technology (available from Invitrogen Life Technologies, Carlsbad, Calif.) which is disclosed in U.S. Pat. Nos. 5,888,732 and 6,277,608, and U.S. Patent Application Publications 2001283529, 2001282319 and 20020007051, all of which are incorporated herein by reference. The GATEWAY™ Cloning Technology Instruction Manual, which is supplied by Invitrogen, also provides concise directions for routine cloning of any desired DNA into a vector comprising operable plant expression elements.

As used herein, "exogenous DNA" refers to DNA which does not naturally originate from the particular construct, cell or organism in which that DNA is found. Recombinant DNA constructs used for transforming plant cells will comprise exogenous DNA and usually other elements as discussed below. As used herein "transgene" means an exogenous DNA that has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation that was transformed with the exogenous DNA.

As used herein "gene" or "coding sequence" means a DNA sequence from which an RNA molecule is transcribed. The RNA may be an mRNA that encodes a protein product, an RNA which functions as an anti-sense molecule, or a structural RNA molecule such as a tRNA, rRNA, or snRNA, or other RNA. As used herein "expression" refers to the combination of intracellular processes, including transcription and translation, undergone by a DNA molecule, such as a structural gene to produce a polypeptide, or a non-structural gene to produce an RNA molecule.

As used herein "promoter" or "5' regulatory region" means a region of DNA sequence that is essential for the initiation of transcription of RNA from DNA. Promoters are located upstream of DNA to be translated, have regions that act as binding sites for RNA polymerase and have regions that work with other factors to promote RNA transcription.

As is well known in the art, recombinant DNA constructs typically also comprise other regulatory elements in addition to a promoter, such as but not limited to 3' untranslated regions (such as polyadenylation sites), transit or signal peptides and marker genes elements. For instance, see U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Patent Application Publication 2002/0192813A1 which discloses 5', 3' and intron elements useful in the design of effective plant expression vectors, U.S. patent application Ser. No. 09/078,972 which discloses a coixin promoter, and U.S. patent application Ser. No. 09/757,089 which discloses a maize chloroplast aldolase promoter, all of which are incorporated herein by reference.

In some aspects of the invention it is preferred that the promoter element in the DNA construct should express in a constitutive manner. In other aspects, it is preferred that the promoter element in the DNA be capable of causing sufficient expression to result in the production of an effective amount of a desired gene under particular conditions, for example, at a particular time in development or in a particular tissue. By avoiding continuous high-level expression of transgenes, any undesired effects caused by continual over-expression of transgenes, or ectopic expression in various tissues or at various times, can be minimized or eliminated.

During transformation, exogenous DNA may be introduced randomly, i.e. at a non-specific location, in the plant genome. In some cases, it may be useful to target heterologous DNA insertion in order to achieve site-specific integration, e.g. to replace an existing gene in the genome. In some other cases it may be useful to target a heterologous DNA integration into the genome at a predetermined site from which it is known that gene expression occurs. Several site-specific recombination systems exist which are known to function in plants include Cre/lox as disclosed in U.S. Pat. No. 4,959,317 and FLP/FRT as disclosed in U.S. Pat. No. 5,527,695, both incorporated herein by reference.

Constructs and vectors may also include a transit peptide for targeting of a gene target to a plant organelle, particularly to a chloroplast, leucoplast or other plastid organelle. For a description of the use of a chloroplast transit peptide see U.S. Pat. No. 5,188,642, incorporated herein by reference.

In practice DNA is introduced into only a small percentage of target cells in any one experiment. Marker genes are used to provide an efficient system for identification of those cells that are stably transformed by receiving and integrating a transgenic DNA construct into their genomes. Preferred marker genes provide selective markers that confer resistance to a selective agent, such as an antibiotic or herbicide. Potentially transformed cells are exposed to the selective agent. In the population of surviving cells will be those cells where, generally, the resistance-conferring gene has been integrated and expressed at sufficient levels to permit cell survival. Cells may be tested further to confirm stable integration of the exogenous DNA. Useful selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS; CP4). Examples of such selectable markers are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Protein and Polypeptide Molecules—Polypeptides of the present invention that represent whole proteins or at least a sufficient portion of the entire protein to impart the relevant biological activity of the protein, e.g. increased yield or increased tolerance to water-deficit. The term "protein" also includes molecules consisting of one or more polypeptide chains. Thus, a polypeptide useful in the present invention may constitute an entire gene product or one or more functional portions of a natural protein that provides a desired agronomic trait.

Homologs of the polypeptides imparting a desired trait or phenotype may be identified by comparison of the amino acid sequence of the polypeptide to amino acid sequences of polypeptides from the same or different plant sources, e.g. manually or by using known homology-based search algorithms such as those commonly known and referred to as BLAST, FASTA, and Smith-Waterman.

A further aspect of the invention comprises functional homologous proteins which differ in one or more amino acids from those of a first polypeptide provided herein as the result of one or more of the well-known conservative amino acid substitutions, e.g. valine is a conservative substitute for alanine and threonine is a conservative substitute for serine. When such a homologous protein is expressed in a transgenic plant, the homologous protein will affect the transgenic plant in a substantially equivalent manner as the first polypeptide.

Transformation Methods and Transgenic Plants—Methods and compositions for transforming plants by introducing an exogenous DNA into a plant genome in the practice of this invention can include any of the well-known and demonstrated methods. Preferred methods of plant transformation are microprojectile bombardment as illustrated in U.S. Pat. Nos. 5,015,580; 5,550,318; 5,538,880; 6,160,208; 6,399,861 and 6,403,865 and Agrobacterium-mediated transformation as illustrated in U.S. Pat. Nos. 5,635,055; 5,824,877; 5,591,616; 5,981,840 and 6,384,301, all of which are incorporated herein by reference. Immature embryos that are useful in the art of transformation are isolated approximately 10 to 14 days post-pollination. The method is also useful for the isolation of embryos from ears aged 15 days or greater post-pollination.

Transformation methods of this invention to provide plants with any desired phenotype resulting from transgene expression are preferably practiced in tissue culture on media and in a controlled environment. "Media" refers to the numerous liquid, solid, or semi-solid nutrient mixtures that are used to grow cells in vitro, that is, outside of the intact living organism. Recipient cell targets include, but are not limited to, meristem cells, callus, immature embryos and gametic cells such as macrospores, pollen, sperm and egg cells. One skilled in the art would know that the type of media and times of transfer used for propagation and regeneration may vary yet still produce identical or substantially identical results.

As used herein a "transgenic" organism is one whose genome has been altered by the incorporation of foreign genetic material or additional copies of native genetic material, e.g. by transformation or recombination. As used herein "transgenic plant" means a plant or progeny plant of any subsequent generation derived therefrom, wherein the DNA of the plant or progeny thereof contains an introduced exogenous DNA not originally present in a non-transgenic plant of the same strain. The transgenic plant may additionally contain sequences that are native to the plant being transformed, but wherein the exogenous DNA has been altered in order to change the level or pattern of expression of the gene.

As used herein an "$R_o$ transgenic plant" is a plant which has been directly transformed with an exogenous DNA or has been regenerated from a cell or cell cluster which has been transformed with an exogenous DNA. As used herein "progeny" means any subsequent generation, including the seeds and plants therefrom, which is derived from a particular parental plant or set of parental plants; the resultant progeny line may be inbred or hybrid. Progeny of a transgenic plant of this invention can be, for example, self-crossed, crossed to a transgenic plant, crossed to a non-transgenic plant, and/or back crossed. As used herein "crop plants" of interest include, but are not limited to soy, cotton, canola, maize, wheat, sunflower, sorghum, alfalfa, barley, millet, rice, tobacco, fruit and vegetable crops, and turf grass.

The seeds of this invention can be harvested from fertile transgenic plants and be used to grow progeny generations of plants of this invention including a hybrid plant line.

EXAMPLES

Having now generally described the invention, the same will be more readily understood through reference to the following examples that are provided by way of illustration, and are not intended to be limiting of the present invention, unless specified.

Example 1

This example illustrates the use of vacuum excision to isolate maize immature embryos and the production of callus tissue from the isolated embryos.

Two Zea mays lines, a male line and a female line, were prepared for vacuum excision. Ears were collected 10-12 days post pollination and were sterilized by immersion in 80% ethanol. Following a short air-drying, each ear was placed on sterilized aluminum foil and gently rolled on a flat surface. A scalpel was used to slice off the crowns (tops) of the kernels.

Using a sterile vacuum aspirator (see FIG. 1), the immature embryos (IEs) and some surrounding endosperm tissue was excised using a vacuum of about 610 mm Hg by introducing the pipette tip into the apical end of the kernel with a horizontal position of the wide bore pipette tip. Occasionally, sterile medium (e.g., 211 liquid media) was also drawn into the aspirator to propel any bits of tissue in the tubing into the collecting receptacle.

Isolation of Partial and Intact Immature Embryos by Vacuum Isolation

When the excision was completed, the liquid and tissue in the collection vessel was poured out onto solid media and excess solution removed by aspiration. The intact immature embryos were isolated and arranged scutellar side up on solid media. Two types of control experiments were carried out; intact immature embryos were isolated manually using small, sterile spatulas and either A) placed directly onto solid media or B) placed into liquid media and then placed onto solid media. The isolated intact IEs of the male line were placed onto solid 211 media. The isolated intact IEs of the female line were placed onto solid 851 media. The intact IEs were incubated at approximately 27-28° C. and callus formation was observed at about 8-11 days after excision. Callus was transferred to fresh media as needed to maintain growth. Exemplary media are listed in Table 1.

Callus was initiated from vacuum excised explants from both maize lines. Data are shown in Table 2 and Table 3, comparing the callus response from the manually excised versus vacuum excised immature embryos for the two maize lines. As can be seen from the data, a number of vacuum excised explants from both maize lines resulted in the formation of callus tissue.

In other experiments, when the excision was completed, the liquid and tissue in the collection vessel was poured out into a thin layer onto solid media and excess solution (about 2 ml) was removed. Partial immature embryos were selected for callus production. The isolated partial IEs from the male maize line were placed onto solid 211 media and incubated at approximately 28° C. The isolated partial IEs from the female maize line were placed onto solid 851 media and incubated at approximately 28° C. Callus formation for each line was observed at about 8-11 days after excision. Callus was transferred to fresh media as needed to maintain growth. Exemplary media are listed in Table 1.

TABLE 1

Media useful for tissue propagation and regeneration

| Media | Type | Components | pH | Gelling agent* |
|---|---|---|---|---|
| 190 | 1X MS salts | 1X MS Fromm vitamins; 0.15 g/L L-Asparagine; 0.1 g/L myo-inositol; 10 g/L glucose; 20 g/L maltose; 250 mg/L carbenicillin; 100 uM glyphosate | 5.8 | 6 g/L Phytagar |
| 192 | 1X MS salts | 1X MS Fromm vitamins; 3.52 mg/L BAP; 50 mg/L casamino acids; 1.36 g/L proline; 30 g/L sucrose; 250 mg/L carbenicillin; 100 uM glyphosate | 5.6 | 6 g/L Phytagar |
| 211 | 1X N6 basal salts | 1 mg/L 2,4-dichlorophenoxyacetic acid (2-4,D); 1 mg/L thiamine; 0.5 mg/L nicotinic acid; 0.91 g/L L-asparagine monohydrous; 100 mg/L myo-inositol; 0.5 g/L 2-(4-morpholino)-ethane sulfonic acid (MES); 1.6 g/L MgCL2•6H2O; 100 mg/L casein hydrolysate; 0.69 g/L proline; 20 g/L sucrose; 16.9 mg/L silver nitrate | 5.8 | 2 g/L Gelgro agar |
| 217 | 1X N6 basal salts | 1.0 mg/L Thiamine, 0.5 mg/L Nicotinic Acid; 3.52 mg/L BAP; 0.91 g/L asparagine; 0.1 g/L myo-inositol; 0.5 g/L 2-(4-morpholino)-ethane sulfonic acid (MES); 1.6 g/L MgCL2•6H2O; 100 mg/L casein hydrolysate; 0.69 g/L proline; 20 g/L sucrose | 5.8 | 6 g/L Phytagar |
| 600 | 0.5X MS salts | 1X MS vitamins (without myo-inositol); 0.5 mg/L thiamine HCl; 0.115 g/L proline; 10 g/L glucose; 20 g/L sucrose; 3 mg/L 2,4-D; 20 µM silver nitrate; 200 µM acetosyringone | 5.2 | 5.5 g/L low melt agarose |
| 601 | 0.5X MS salts | 0.5X MS vitamins (without myo-inositol); 0.115 g/L proline; 26 g/L glucose; 68.5 g/L sucrose | 5.4 | none |
| 632 | 1X MS salts | 1X MS Fromm vitamins; 0.05 g/L myo-inositol; 60 g/L sucrose; 250 mg/L carbenicillin; 100 mg/L paromomycin | 5.8 | 6 g/L Phytagar |
| 850 | 1X MS salts | 1X MS vitamins; 0.5 mg/L thiamine HCl; 1.38 g/L proline; 30 g/L sucrose; 0.5 g/L casein hydrolysate; 0.5 mg/L 2,4-D; 0.01 mg/L BAP; 100 uM glyphosate; 500 mg/L carbenecillin; 20 uM silver nitrate | 5.8 | 3 g/L phytagel |
| 851 | 1X MS salts | 1X MS vitamins; 1.38 g/L proline; 30 g/L sucrose; 0.5 g/L casein hydrolysate; 0.5 mg/L 2,4-D; 2.2 mg/L picloram; 20 uM silver nitrate | 5.8 | 3.0 g/L phytagel |
| 852 | 0.5X MS salts | 0.5X MS vitamins; 20 g/L sucrose; 0.5 mg/L IBA; 0.5 mg/L 1-naphthalene acetic acid (NAA); 100 uM glyphosate | 5.8 | 3 g/L phytagel |

*Liquid media have the same components as solid media with the exception of a gelling agent. Filtered, reverse-osmosis water was used to prepare media used in the practice of this invention.

TABLE 2

Callus production from vacuum excised explants from a maize male line

| Method | I.E. Size (mm) | # of Kernels | # IE's Excised | # Calli |
|---|---|---|---|---|
| Manual Excision | 2.0-2.2 | 100 | 98 | 95 |
| Manual Excision | 1.8-2.0 | 95 | 88 | 83 |
| Manual Excision | 1.7-1.9 | 107 | 90 | 77 |
| Manual Excision into Liquid | 2.0-2.2 | 92 | 84 | 48 |
| Manual Excision into Liquid | 1.8-2.0 | 100 | 90 | 53 |
| Manual Excision into Liquid | 1.7-1.9 | 90 | 72 | 31 |
| Vacuum Excision | 2.0-2.2 | 98 | 39 | 16 |
| Vacuum Excision | 1.8-2.0 | 100 | 63 | 40 |
| Vacuum Excision | 1.7-1.9 | 100 | 54 | 7 |

TABLE 3

Callus production from vacuum excised explants from a maize female line

| Method | I.E. Size (mm) | # of Kernels | # IE's Excised | # Calli |
|---|---|---|---|---|
| Manual Excision | 1.4-1.6 | 97 | 88 | 88 |
| Manual Excision | 1.3-1.8 | 95 | 85 | 79 |
| Manual Excision | 1.7 | 74 | 45 | 42 |
| Manual Excision into Liquid | 1.4-1.6 | 73 | 62 | 62 |
| Manual Excision into Liquid | 1.3-1.8 | 72 | 56 | 54 |
| Manual Excision into Liquid | 1.7 | 65 | 35 | 33 |
| Vacuum Excision | 1.4-1.6 | 84 | 34 | 28 |
| Vacuum Excision | 1.3-1.8 | 83 | 58 | 51 |
| Vacuum Excision | 1.7 | 80 | 6 | 5 |

Isolation of Intact and Partial Immature Embryos Using a Sieving Unit

Immature embryos of the female maize line were isolated using vacuum excision wherein the aspirator was fitted with an in-line sieving unit. Following excision of the embryos from the ear, approximately 10-15 mls of liquid (e.g., liquid media) were also drawn through the in-line sieving unit to ensure any material in the isolation tube was drawn onto the sieving materials. The in-line sieving unit was then disassembled and the immature embryos and other material on the sieving material were flushed off and collected in a petri dish. The embryos, both partial and intact, were then transferred to solid 851 media and callus was produced.

Isolation of an Immature Embryo Slurry by Vacuum Isolation

A "slurry" of immature embryos of a female maize line, comprising both partial and intact IEs as well as any other material collected from the kernels, was also isolated using vacuum excision, both with and without the in-line sieving unit. When the excision was completed without the sieving unit, approximately 1-2 ml of the liquid and tissue in the collection receptacle, that is, the slurry comprising intact and partial immature embryos, was plated out into a thin layer (thin-plated) onto solid 851 media and incubated at approximately 28° C. When excision was completed using the sieving unit, the unit was disassembled and the collected tissue was released by swirling the sieving layers in liquid media, releasing the trapped tissues and creating a slurry comprising both partial and intact IEs as well as any other material collected from the kernels. The slurry was then thin-plated onto solid 851 media as described.

Using both types of isolation methods, callus formation for each line was observed at about 8-11 days after excision.

Callus prepared from intact IEs, partial IEs or a slurry mixture of immature and mature IEs is regenerated into fertile plants using media and methods of transfer known to those in the art (see also Example 2).

Example 2

This example describes the production of a transgenic plant prepared by transformation of immature embryos isolated using vacuum excision.

Transformation of Intact Immature Embryos

Intact immature embryos were vacuum excised (~610 mm Hg) from a female maize line ears 10-12 days post pollination as described in Example 1 and used for *Agrobacterium* mediated transformation.

*Agrobacterium* was transformed to contain a vector comprising a green fluorescent protein (GFP) marker gene and a CP4 marker gene allowing for herbicide resistance. Excess liquid was removed from the vacuum isolated intact embryos. The embryos were allowed to incubate with the *Agrobacterium* for about 15-20 minutes at room temperature. The intact embryos were removed from the *Agrobacterium* solution, placed onto solid 600 media and allowed to incubate overnight. Following this, the vacuum excised tissues were placed onto solid 850 media for about 3 weeks, followed by about 1 week on solid 192 media, followed by about 2 weeks on solid 190 media, followed by about 3 weeks on solid 190 media, and then a transfer to soil.

Eleven different transgenic events from the vacuum excised tissues were selected for regeneration and one stable transgenic plant exhibiting GFP expression was obtained from the vacuum excised transformed tissue. The plant was allowed to mature and seed was recovered.

Transformation of a Mixture Immature Embryos

Partial and intact immature embryos were vacuum excised (~610 mm Hg) from a female maize line ears 10-12 days post pollination as described in Example 1 and used for *Agrobacterium* mediated transformation. The mixture of partial and intact IEs are exposed to *Agrobacterium* as described above and both intact and partial embryos are removed from the *Agrobacterium* solution and placed into the selection and regeneration processes. Transgenic plantlets are recovered, allowed to mature into fertile transgenic plants and seed may be collected.

Example 3

This example describes the production of a transgenic plant prepared by transformation of callus material prepared from immature embryos isolated using vacuum excision. Two *Zea mays* lines, a representative male and female line, were prepared for vacuum excision as described in Example 1.

Intact Immature Embryos

Callus isolated from intact immature embryos is useful for transformation and regeneration of mature transgenic plants. Intact immature embryos were vacuum excised into the collecting receptacle, and the liquid and tissue in the collection vessel was poured out into a thin layer onto solid media. In other experiments, the sieving unit was used to collect the intact IEs. Following either excision method, intact immature embryos were selected for callus production. The isolated IEs from the male maize line were placed onto solid 211 media and incubated at approximately 28° C. The isolated IEs from the female maize line were placed onto solid 851 media and incubated at approximately 28° C. Callus formation for each line was observed at about 8-11 days after excision. Callus derived from intact IEs is useful for transformation, regeneration and production of fertile, transgenic plants.

Partial Immature Embryos

Callus isolated from partial immature embryos is also useful for transformation and regeneration of mature transgenic plants. Partial immature embryos were vacuum excised either directly into the collecting receptacle or, in some experiments, the IEs were collected on the sieving unit. The partial IEs isolated from either method were used for callus production. Callus prepared from partial IEs was subcultured and grown to increase the amount of tissue useful for transformation and/or regeneration into mature transgenic plants. The callus tissue was exposed to *Agrobacterium* comprising genes of interest for transfer to the recipient genome. Following culturing and selection on media appropriate for the maize line employed, transformed cells are selected and plantlets will be regenerated. The plantlets are allowed to mature and transgenic seed may be collected.

Intact and Partial Immature Embryos

In other experiments, the material used for transformation was derived from a slurry of intact and partial immature embryos. Agrobacterium was transformed to contain various vectors comprising an NPTII marker gene allowing for paromomycin resistance. Callus derived from the slurry of intact and partial immature embryos was exposed to the *Agrobacterium* for transformation. Callus exhibiting resistance to paromomycin was recovered and regenerated into plantlets, with greater than 10% of the callus forming transgenic plantlets. The transgenic plantlets are grown under greenhouses into mature plants and seed may be collected.

What is claimed is:
1. A method for isolating embryogenic tissue from a monocot kernel comprising
   a) exposing endosperm containing embryogenic tissue; and
   b) excising said embryogenic tissue from tissue of said monocot kernel by aspiration.

2. The method of claim 1 wherein the monocot kernel is from a variety of maize.

3. The method of claim 1 wherein said embryogenic tissue comprises an immature embryo.

4. The method of claim 3 wherein said embryogenic tissue comprises an intact immature embryo.

5. The method of claim 3 wherein said embryogenic tissue comprises a partial immature embryo.

6. The method of claim 1 wherein embryogenic tissue is isolated from a number of kernels on an ear of maize.

7. The method of claim 6 wherein the embryogenic tissue is comprised within a mixture of intact and partial embryos.

8. The method as in claim 1 further comprising propagating the excised embryogenic tissue.

9. The method of claim 6 wherein the propagating is the production of callus tissue.

10. The method of claim 6 wherein the propagating comprises the regeneration of a plant.

11. The method of claim 10 wherein the regenerated plant is fertile.

12. A method for transforming a variety of monocot plant comprising
    a) isolating embryogenic tissue from tissue of a kernel of said variety of monocot plant by vacuum excision,
    b) introducing a recombinant DNA construct into the genome of a cell of said embryogenic tissue or a cell derived from said embryogenic tissue, and
    c) growing a transformed monocot plant from said transformed cell.

13. The method of claim 12 wherein the embryogenic tissue comprises an immature embryo.

14. The method of claim 13 wherein the immature embryo is intact or partial.

15. The method of claim 12 wherein a plurality of immature embryos are isolated from a number of kernels on an ear of maize.

16. The method of claim 15 wherein the plurality of immature embryos is a mixture of partial and intact embryos.

17. The method of claim 12 wherein the transformed monocot plant is fertile.

\* \* \* \* \*